United States Patent [19]
Kawasaki et al.

[11] Patent Number: 5,433,724
[45] Date of Patent: Jul. 18, 1995

[54] COMPRESSIVE HEMOSTATIC BELT

[75] Inventors: Atsuko Kawasaki, Akashi; Takefumi Nakashita, Kobe; Yoshiharu Inui, Takarazuka; Shinichi Hori, Sakai; Toshiaki Sakaki, Kakogawa; Miyo Miki, Kobe, all of Japan

[73] Assignee: Sumitomo Rubber Industries, Ltd., Kobe, Japan

[21] Appl. No.: 214,663

[22] Filed: Mar. 18, 1994

Related U.S. Application Data

[63] Continuation of Ser. No. 872,708, Apr. 22, 1992, abandoned.

[30] Foreign Application Priority Data

| Apr. 23, 1991 | [JP] | Japan | 3-122351 |
| Feb. 6, 1992 | [JP] | Japan | 4-020793 |
| Feb. 19, 1992 | [JP] | Japan | 4-031236 |
| Feb. 28, 1992 | [JP] | Japan | 4-009759 U |
| Mar. 26, 1992 | [JP] | Japan | 4-067682 |

[51] Int. Cl.[6] .................................. A61B 17/12
[52] U.S. Cl. .................................. 606/202; 128/686
[58] Field of Search .................. 606/201–204; 128/677, 686

[56] References Cited

U.S. PATENT DOCUMENTS

| 2,104,758 | 1/1938 | Poppen . | |
| 2,344,021 | 3/1944 | Bouziane | 606/201 |
| 3,171,410 | 3/1965 | Towle, Jr. et al. | 606/202 |
| 3,467,085 | 9/1969 | Cormier . | |
| 3,633,567 | 1/1972 | Sarnoff . | |
| 3,670,735 | 6/1972 | Hazlewood . | |
| 4,275,718 | 6/1981 | Jungmann . | |
| 4,800,900 | 1/1989 | French | 606/202 |
| 4,829,994 | 5/1989 | Kurth | 128/96.1 |

FOREIGN PATENT DOCUMENTS

| 0462088 | 12/1991 | European Pat. Off. . | |
| 910340 | 6/1946 | France . | |
| 1388168 | 12/1964 | France | 606/203 |
| 571744 | 2/1933 | Germany . | |
| 56336 | 4/1990 | Germany . | |
| 4-11010 | 1/1992 | Japan . | |
| 1206605 | 9/1970 | United Kingdom . | |

Primary Examiner—Stephen C. Pellegrino
Assistant Examiner—William Lewis
Attorney, Agent, or Firm—Nikaido, Marmelstein, Murray & Oram

[57] ABSTRACT

A compressive hemostatic belt which is easily operable and thrown away after use, incorporates a strip (1) in the form of a nonstretch or low-stretch textile fabric, and a bag (5) expansible by being filled with fluid that is attached to the strip at a predetermined position by an attaching device. A pump (8) and a pressure gauge (9) are connected to the bag (5) attached at the predetermined position on the strip (1), so that the bag is expanded by operating the pump so as to fill the bag (5) with a suitable fluid while watching the pressure gauge (9). The bag thus presses down on an area (A) where bleeding is to be stopped.

6 Claims, 5 Drawing Sheets

COMPRESSIVE HEMOSTATIC BELT

This application is a continuation application of Ser. No. 07/872,708 filed Apr. 22, 1992, now abandoned.

BACKGROUND OF THE INVENTION

1. Field Of The Invention

The present invention relates to a compressive hemostatic belt used to stop bleeding from a catheter insertion wound upon completion of an arterial catheter examination.

2. Prior Art

Recently, arterial catheter examinations have been made for contrast medium-using diagnosis of hearts or cerebral blood vessels. Cardiac catheter examinations are performed through surgical. In most cases, the so-called catheter puncture method which moves a catheter from the femoral artery or vein in the inguinal region to the heart is used.

In this examination method, a contrast medium or various medicines are injected through the catheter puncturing the femoral artery or vein in the inguinal region, or other various preoperative and postoperative examinations are conducted. In this connection, there is a need to compress the catheter insertion wound for a relatively long time in order to stop the bleeding from the catheter insertion wound resulting from the extraction of the catheter from the femoral artery or vein in the inguinal region.

With the compressive hemostatic method for catheter insertion wounds, it has been common practice for a doctor or nurse to manually compress a catheter insertion wound for about 15 minutes, apply gauze to the catheter insertion wound, apply 3 or 4, 70-cm long 5-cm wide fabric adhesive plaster over the gauze to compress the catheter insertion wound from above the gauze, placing a sand bag having a controlled weight of 500-1000 kg, and affixing the sand bag against moving by the fabric adhesive plaster. The compression is maintained for 12-24 hours.

However, in the conventional method described above, the use of adhesive plaster as means for fixing the gauze applied to the catheter insertion wound and also affixing the sand bag placed thereon after extraction of the catheter has drawback in that the patient often experiences a stiffening feel, pain and/or itching. The conventional method can also cause dermatitis and vesicular exanthema.

The sand bag tends to slip off when the patient lying on his back tilts his body even slightly. Such a deviation of the sand bag results in the sand bag deviating from the compressed area, making the hemostatic effect and thus leading to other drawbacks, such as ecchymoma.

On the other hand, in order to solve such problems, Japanese Patent Application Disclosure No. 92746/1985 or Japanese Patent Application Disclosure No. 198139/1985 have suggested a compressive hemostatic belt formed of stretch fabric as part of a compressive hemostatic means for catheter insertion wounds to replace the adhesive plaster and sand bag.

Such a compressive hemostatic belt, however, is constructed so as to be difficult for a user to wrap it and to visually ascertain the level of its compressive force on the catheter insertion wound. Thus, it is necessary for him to rewrap the belt when adjusting the compressive force. All in all the loading state of the belt is unstable.

Further, since the belt uses an expensive stretch textile fabric, its production cost is very high, making away difficult to throw it after use especially when there is a hygienic problem of causing infectious diseases due to the adhesion of blood to the fabric. Therefore, to prevent such hemoinfectious diseases, after each use of the compressive hemostatic belt, it is washed and sterilized, imposing limitations not only from a hygienic standpoint but also from the standpoint of enhancing labor savings for nurses.

SUMMARY OF THE INVENTION

The present invention provides a compressive hemostatic belt comprising a strip of nonstretch or low-stretch fabric, and a bag adapted to be expanded by being filled with fluid, wherein the bag is attached to the strip at a predetermined position thereon.

The bag attached to the strip at the predetermined position has a pump and a pressure gauge connected thereto through a check valve. The operator operates the pump while watching the pressure gauge filling the bag with fluid so as to expand the bag and compress an area where bleeding is to be stopped. Since a nonstretch or low-stretch textile fabric is used for the strip, the development of a stiffening feel, pain or itch can be avoided, and dermatitis or bubbles are prevented. The use of the bag which is filled with fluid as compressing means provides a narrower range of compression, ensuring a hemostatic function of compressing only a catheter insertion wound while causing almost no compressive feeling to be transmitted to other areas.

Further, since the pressurizing mechanism is constructed by connecting, through a check valve, a pump and a pressure gauge to the bag which is expansible by being filled with fluid, it is possible to adjust the compressive force to be applied to a catheter insertion wound and to maintain that adjusted force for a long time by the check valve. Further, since compressing and fixing are simultaneously effected by the bag which is expansible by being fixed with fluid, there is provided a compressive hemostatic belt whose operability is satisfactory, which does not require a sand bag or the like, and is compact and easy to carry about. The components other than the pump and pressure gauge are much cheaper than the parts of conventional device allowing the belt to be thrown away once it has been used. Thus, the noteworthy goals of improving health control and promoting labor saving are attained.

A rigid case for preventing the bag from expanding to the side opposite to the area where bleeding it to be stopped may be installed, if necessary, between the bag and the strip. This rigid case has an inner flange around its open end to surround the bag or balloon. The inner flange of the rigid case may be a separate body with the intended compression area cut out in doughnut form, and may be attached to the open end of the rigid case.

With the inner flange formed around the open end of the rigid case to surround the balloon, the balloon can be reliably expanded to the area where bleeding is to be stopped while the inner flange of the rigid case prevents the balloon from deviating outside. Therefore, there is no possibility of the bag from deviating the predetermined position, and the area can be positively compressed by the bag so as to provide a perfect hemostatic effect. Further, if the inner flange of the rigid case is a separate body with the compressive area cut out to suit the affected area where bleeding is to be stopped and is attached to the open end of said rigid case, doughnut-shaped inner flanges with various compressive areas cut out may be prepared, making it possible to adjust the compressive area and to prevent stagnation otherwise caused by wide area compression.

Since any compressive hemostatic belt would be applied to a patient who is lying on his side upon completion of a catheter examination, the wrapping operation of the strip can be difficult to perform depending upon the location where the belt is applied. Further, conventionally designed strips tend to develop wrinkles and kinks in its portion applied to the patient's waist and hip. Such wrinkles and can give the patient an unpleasant feeling and the compression of the wound can be made insufficient by the wrinkles being smoothed after the wrapping of the strip. If the strip is wrapped with a greater force in an effort to smooth the wrinkles, the wound is compressed more than necessary.

Another object of the invention is to provide a compressive hemostatic belt which does not develop wrinkles when applied and which is capable of exerting a stabilized compressive force.

To achieve the object, the invention attaches a reinforcing sheet to the portion of the strip which covers the area of the body extending from the waist to the hip when the belt is applied.

The reinforcing sheet is preferably 10–90 cm long and is placed laterally of the pocket of the strip.

The provision of the reinforcing sheet on the portion of the strip which covers the area of the patient's body extending from the waist to the hip prevents wrinkles or kinks from developing in this portion when the strip is wrapped. Thus, the strip can be reliably wrapped without having to exert a very great force. The a degree of tightening which is suited to the patient can be obtained.

By suitably changing the place for applying the reinforcing sheet and the reinforcing area, various degrees of tightening suited to persons of various body types, such as children, slim persons and fat persons can be obtained.

Thereby, the wound can be reliably compressed and there is no possibility of giving the patient an unpleasant feeling due to kinks or the like. Further, since the force required for wrapping is not so great, the labor of nurses or the like for installing the belt can be reduced, and stagnation and ecchymona due to greater compression than necessary can be avoided.

DESCRIPTION OF THE PREFERRED EMBODIMENTS

The invention will now be described with reference to the drawings.

Figure 1:
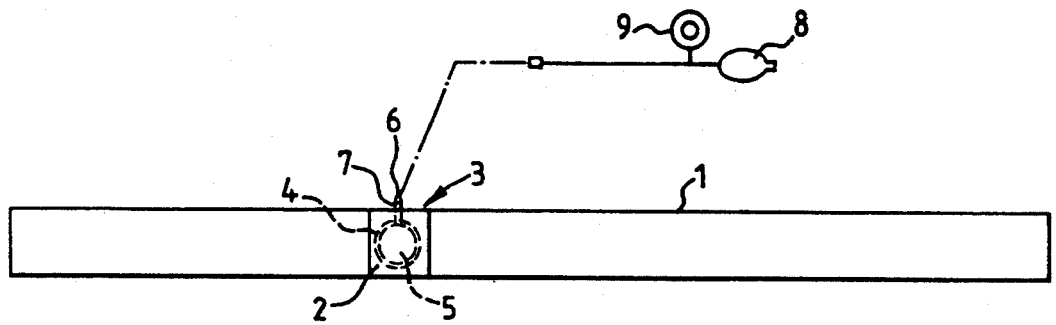
FIG. 1 is a front view showing a compressive hemostatic belt according to an embodiment of the present invention.
Figure 2:
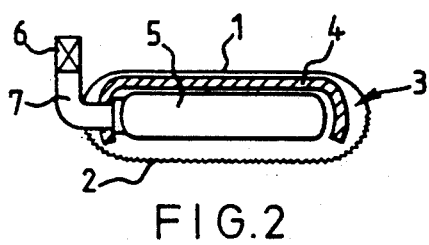
FIG. 2 is a longitudinal sectional view taken at the position of the pocket of the compressive hemostatic belt.

FIGS. 1 and 2 show a compressive hemostatic belt according to an embodiment of the invention. The numeral 1 denotes a strip made of a nonstretch or low-stretch textile fabric formed with a pocket 3 by sewing a pocket fabric 2 in the form of a stretch textile fabric thereto at a predetermined position. The numeral 4 denotes a rigid case which is a bowl shaped rigid member made of synthetic resin or the like. The rigid case is received in the pocket 3 of the strip 1 with its open side directed to the pocket fabric 2. The numeral 5 denotes a bag which can be expanded by being filled with a suitable fluid (a gas, such as air or nitrogen gas or a liquid including a gel). The bag (for example) is a balloon made of rubber, received in the pocket 3 of the strip 1 through the rigid case 4, with a fluid feed tube 7 projecting outward and having a check valve 6. The fluid feed tube 7 of the balloon 5 has a manually operable pump 8 and a pressure gage 9 connected thereto. Thus, by operating the pump 8 while watching the pressure gauge 9, an operator can fill fluid into the balloon 5 through the fluid feed tube 7 to expand the balloon 5.

The way of using the compressive hemostatic belt of the present invention will now be described.

Figure 3:
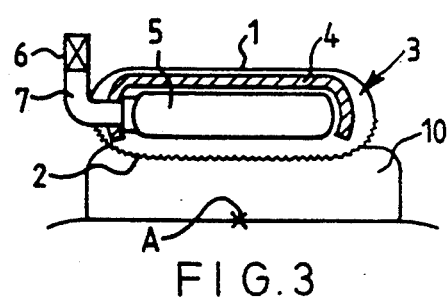
FIG. 3 is a longitudinal sectional view showing the state existing before balloon expansion, taken at the pocket position, when the compressive hemostatic belt is used.
Figure 4:
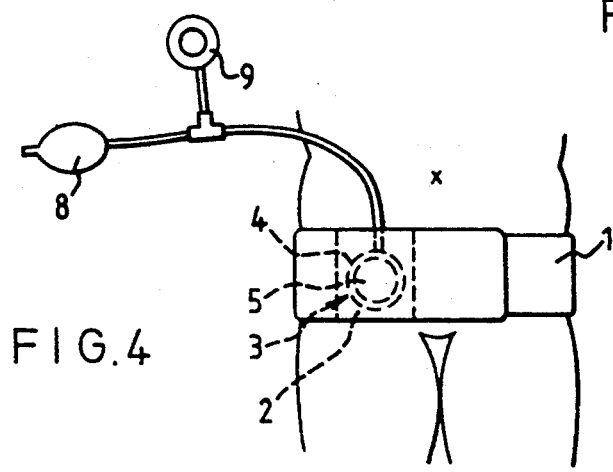
FIG. 4 is an explanatory view showing an example of the way the compressive hemostatic belt is wrapped.
Figure 5:
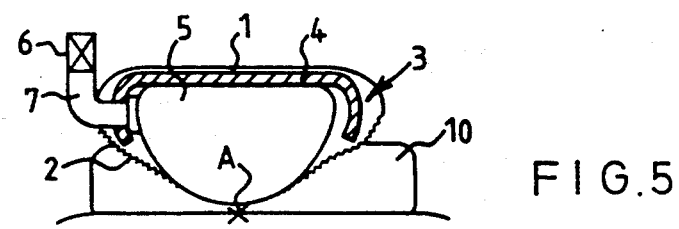
FIG. 5 is a longitudinal sectional view showing the state existing during balloon expansion, taken at the pocket position, when the compressive hemostatic belt is used.

As shown in FIG. 3, gauze 10 is placed on a catheter insertion wound A after extraction of the catheter, and then the belt is placed thereon such that the pocket fabric 2 of the pocket 3 receiving the balloon 5 is directed to the gauze 10. Then, for example, as shown in FIG. 4, the strip 1 is wrapped around the waist of the patient with more than one turn, the end being fixed in place by utilizing fixing means, such as adhesive plaster.

Upon completion of the wrapping of the strip 1, the manually operable pump 8 and pressure gauge 9 are connected to the fluid feed tube 7 of the balloon 5 and the pump 8 is operated while watching the pressure gauge 9, so as to fill the balloon 5 with the fluid. The balloon 5 expands toward the catheter insertion wound A with the rigid case 4 preventing the balloon 5 from expanding toward the side opposite to the catheter insertion wound A. The catheter insertion wound A is thus compressed through the gauze 10, and at the same time the strip 1 is firmly secured to the patient.

At this time, an adjusting the compressive force by changing the amount of liquid or gas injected into the balloon 5 in accordance with the bodily shape of the patient using the pump 8 while watching the pressure gauge 9, a compressively hemostatic effect suited for the patient can be obtained. The adjusted compressive force can be maintained for a long time by the check valve 6. It is also possible to employ automatic compressive force control using a computer, as the need arises.

In addition, in the above embodiment, the strip 1 is described as being formed from a nonstretch textile fabric, but it may be formed of a low-stretch textile fabric. The pocket 3 is described as being formed by sewing a fabric 2 which is a stretch textile fabric. It may be formed by fabricating the strip 1 in a bag form to provide a pocket 3 at a predetermined position to receive the rigid case 4 and balloon 5 therein. Even in the case where the strip 1 is fabricated in bag form using a nonstretch or low-stretch textile fabric, as described above, the compressive force exerted by the expansion of the balloon 5 on the catheter insertion wound A is sufficient. If, however, the surface of the pocket 3 of the strip 1 receiving the balloon 5 opposite to the catheter insertion wound A is made of stretch fiber, the compressive force on the catheter insertion wound A can be increased.

In the above embodiment, the balloon 5 is received in the pocket 3 of the strip 1 through the rigid case 4 for preventing the expansion of the balloon 5 toward the side opposite to the catheter insertion wound A. However, the balloon 5 may be received by itself in the pocket 3 of the strip 1. In this case, the balloon 5 can be expanded toward the catheter insertion wound A while the strip 1 prevents it from expanding toward the side opposite to the catheter insertion wound A.

When the balloon 5 is expanded with liquid, as compared with the case of expanding it with gas, the liquid tends to leak less through the balloon 5 and the check valve 6 attached thereto. Even if the liquid does leak, the leakage can be more easily detected and the compressive force can be maintained at a constant value.

Figure 12:
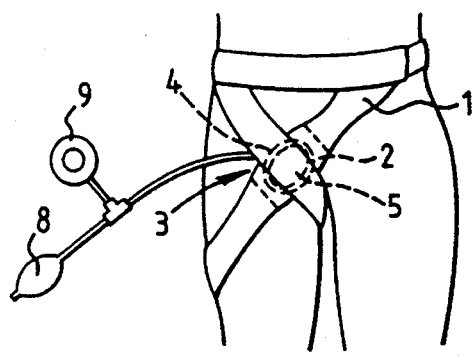
FIG. 12 is an explanatory view showing an example of the way the compressive hemostatic belt is wrapped.

In the above embodiment, as shown in FIG. 4, the strip 1 is wound at right angles with the body axis. However, the invention is not limited thereto. Besides the wrapping method shown in FIG. 4, the strip 1 may be wrapped cross-wise as shown in FIG. 12.

According to the compressive hemostatic belt, since the catheter insertion wound A can be compressed by utilizing the expansion of the balloon 5 as described above, the catheter insertion wound A itself can be compressed, with almost no compressed feeling transmitted to other areas of the patient's body.

Further, since a nonstretch or low-stretch fabric is used for the strip 1, the occurrence of a stiff feeling or itch is avoided, and the dermatitis and bubbles are prevented.

The above relates to an embodiment of the invention but the invention is not limited thereto and various changes in engineering design are possible within the scope of the invention.

First, while the preceding embodiment uses rubber as a material for the bag, rubber may be replaced by hardly fluid-permeable materials which are soft at ordinary temperature. This includes thermoplastic materials, such as polyethylene terephthalate, soft vinyl chloride, vinylidene chloride, nylon 6, nylon 6—6, nylon 12, and composite materials such as polyethylene terephthalate and polyethylene.

Figure 6:
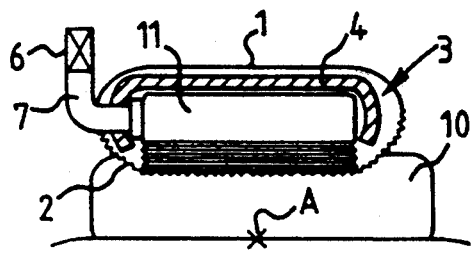
FIG. 6 is a longitudinal sectional view showing the state existing before bag expansion taken at the pocket position in a compressive hemostatic belt according to another embodiment of the invention using a separate bag.
Figure 7:
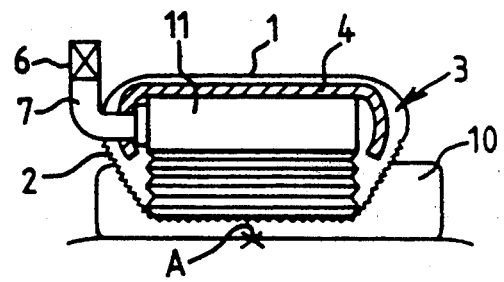
FIG. 7 is a longitudinal sectional view showing the state existing during bag expansion, taken at the pocket position on the compressive hemostatic belt of FIG. 6.

FIGS. 6 and 7 show an embodiment using a bag 11 made of a hardly fluid-permeable material which is soft at ordinary temperature, other than rubber. The bag 11 is in the form of bellows which can be expanded by being filled with fluid and as shown in FIG. 6. The bag 11 is received in its folded state in the pocket 3 of the strip 1 through the rigid case 4. By filling the bag 11 with fluid through the fluid feed tube 7, the bag 11 is expanded as shown in FIG. 7 to compress the catheter insertion wound A through the gauze 10. In addition, in this embodiment, the rigid case 4 and the bag 11 are separately formed, but they may be integrally formed.

Figure 8:
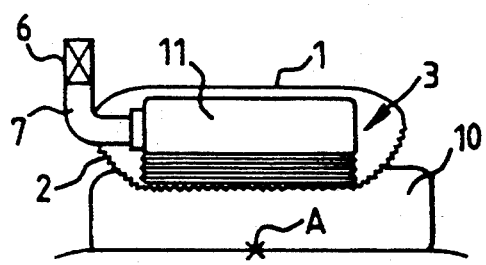
FIG. 8 is a longitudinal sectional view showing the state existing before bag expansion, taken at the pocket position on a compressive hemostatic belt according to another embodiment of the invention not using a rigid case.
Figure 9:
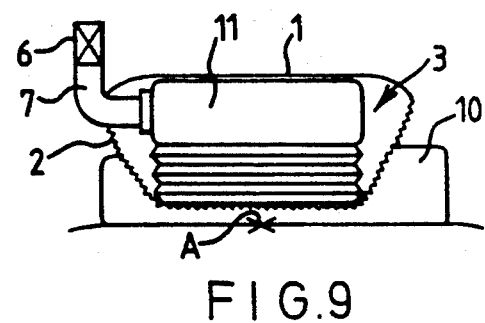
FIG. 9 is a longitudinal sectional view showing the state existing during bag expansion, taken at the pocket position on the compressive hemostatic belt of FIG. 9.

Further, in the above embodiment, the bag 11 is received in the pocket 3 of the strip 1 through the rigid case 4 so as to prevent the bag from expanding toward the side opposite to the catheter insertion wound. However as shown in FIG. 8, even if the bag 11 is received by itself in the pocket 3 of the strip 1 without the rigid case 4 intervening therebetween, the bag 11 is prevented from expanding toward the side opposite to the catheter insertion wound A since the strip 1 is a nonstretch or low-stretch textile fabric. Thus, as shown in FIG. 9, the bag 11 is allowed to expand only toward the catheter insertion wound A, exerting a sufficient compressive force to compress the catheter insertion wound A. Thus, the bag 11 may be received in the pocket 3 of the strip 1 through the rigid case 4 as the need arises.

In the above embodiment, a stretch textile fabric is used for the pocket fabric 2 forming the pocket 3 in the strip. However the pocket fabric 2 may be a nonstretch or low-stretch textile fabric provided that the pocket 3 is formed large enough to allow the balloon 5 or bag 11 received therein to expand freely.

Figure 10:
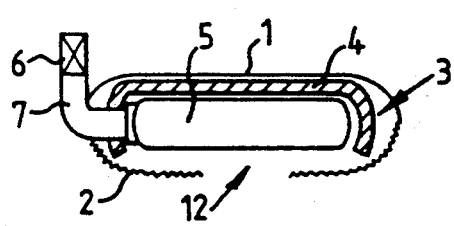
FIG. 10 is a longitudinal sectional view showing the state existing before balloon expansion, taken at the pocket position on a compressive hemostatic belt according to another embodiment of the invention having a passage formed in a pocket fabric.
Figure 11:
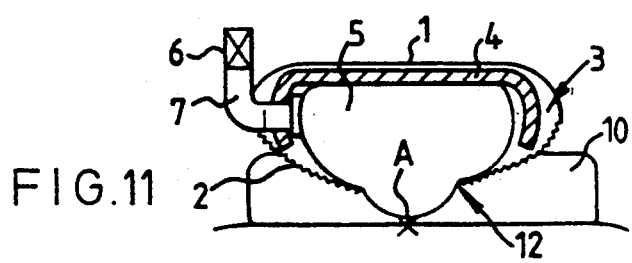
FIG. 11 is a longitudinal sectional view showing the state existing during balloon expansion, taken at the pocket position on the compressive hemostatic belt of FIG. 10.

Further, as shown in FIG. 10, the pocket 3 may be formed with an opening 12 to expose the balloon 12. If the pocket 3 is formed with the opening 12, as shown in FIG. 11 it is possible to allow the balloon 5 to expand such that it partly projects through the opening 12, thereby increasing the compressive force on the catheter insertion wound A.

In the above embodiment, the balloon 5 or bag 12 is received in the pocket 3 of the strip 1 to thereby attach the balloon 5 or bag 11 to the strip. However the balloon 5 or bag 11 may be attached to the strip 1 at a predetermined position by fastening means such as an adhesive agent or fastener.

Another embodiment of the invention will now be described with reference to FIGS. 13 through 16.

Figure 14:
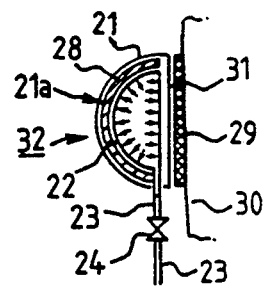
FIG. 14 is a longitudinal sectional view showing the compressive portion of the compressive hemostatic belt.
Figure 13:
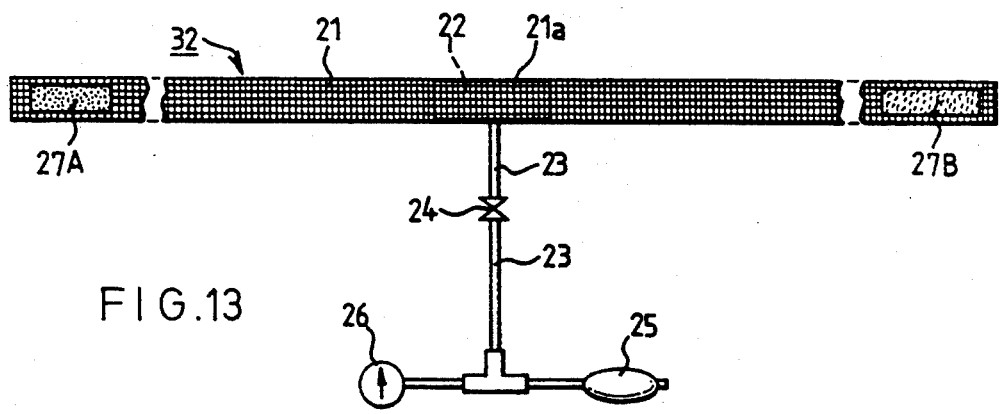
FIG. 13 is a front view of a compressive hemostatic belt according to another embodiment of the invention.

A compressive hemostatic belt 31 according to the invention comprises a bag-like strip 21 formed of a knit fabric, woven fabric or nonwoven fabric of nonstretch fiber (i.e., cotton or polyester) or a nonstretch or low-stretch fiber (i.e., polyamide), and a rubber balloon 22 inserted in a pocket 21a formed at a predetermined position on the strip 21 through a bowl 28 of synthetic resin, wherein the two members form compressive means for an area where bleeding is to be stopped (e.g., a catheter insertion wound.) The strip 21 may be formed in its entirety of a knit fabric or woven fabric of nonstretch or low-stretch fiber or may have its portion opposed to the catheter insertion wound 30 made of stretch fiber, e.g. (LIKURA (phonetically) an elastic fiber produced by Du pont de Nemours & Co.). If the portion opposed to the catheter insertion wound 30 is made of stretch fiber as described above, the rubber balloon 22 can be expanded more easily than when the whole of the strip 21 is made of nonstretch fiber, and the compressive force on the insertion wound 30 is further increased. The rubber balloon 22 may be received in the pocket 21a of the strip 21 with the check valve 24 exposed. In order to prevent the rubber balloon 22 from expanding toward the side opposite to the insertion wound 30, as shown in FIG. 14 it may be received in the pocket 21a of the strip 21 through a bowl 28 made of synthetic resin. A manually operable air pump 25 and a pressure gage 26 are connected through the check valve 24 to the air feed tube 23 leading to the rubber balloon 22. By operating the air pump 25 while watching the pressure gage 26, the pressure in the rubber balloon 22 is maintained at a value suitable for compressing the insertion wound 30 for a predetermined period of time. An automatic pressure control system using a computer may be employed as the need arises.

Figure 15:
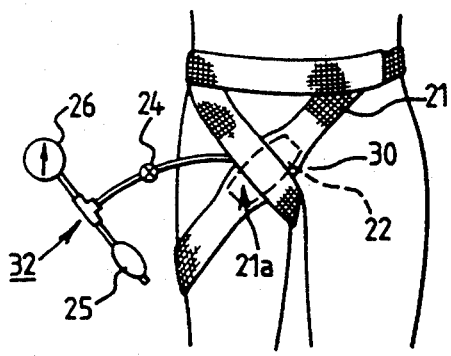
FIG. 15 is an explanatory view showing how the compressive hemostatic belt is used.
Figure 16:
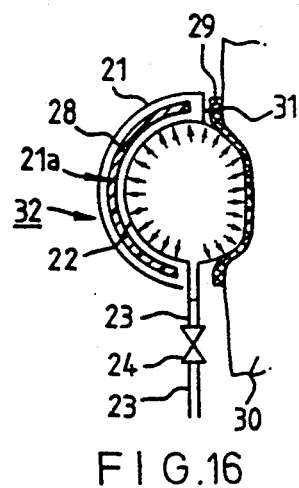
FIG. 16 is a longitudinal sectional view showing the compressive portion of the compressive hemostatic belt during use.

Another embodiment wherein upon completion of heart catheter examination, the compressive hemostatic belt according to the invention is used to stop bleeding from the insertion wound 30 in the inguinal region, will now be described with reference to FIGS. 15 and 16.

Gauze 29 is placed on the insertion wound 30 subsequent to extraction of the catheter and the compressive hemostatic belt is wrapped thereon. That is, the pocket 21a of the strip 21 having the balloon 22 received therein is placed on the insertion wound 30, and the strip 21 is passed from the inguinal region of the lower limb over the outer side, back side and inner side of the thigh and from the crotch over the front side of the thigh and crossed X-wise on the inguinal region. The remaining portion is wrapped in one or more layers around the trunk with the remaining portion of the strip 21 being fixed in position by fixing means such as directionless fabric fasteners 27A and 27B. Thereafter, the air pump 25 is operated while watching the pressure gauge 26 to expand the rubber balloon 22, as shown in FIG. 25, to produce a compressive force to position and fix the compressive portion 31 on the insertion wound 30. The above description refers to an example in which the present inventive device is used to stop bleeding from the insertion wound 30 in the inguinal region of the lower limb. However, by controlling the abutting position of the rubber balloon 22 and the wrapping position of the compressive hemostatic belt 32, the compressive hemostatic effect can be exerted in any portion of the body other than the inguinal region of the lower limb.

Another embodiment of the invention will now be described with reference to the drawings.

Figure 17:
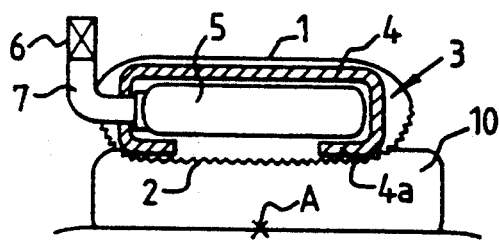
FIG. 17 is a longitudinal sectional view showing the compressive portion after injection of fluid into acompressive hemostatic belt according to another embodiment of the invention.
Figure 18:
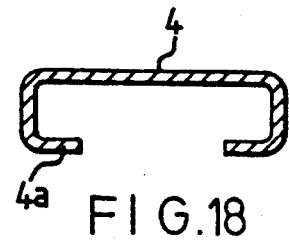
FIG. 18 is a longitudinal sectional view of a rigid case used for the compressive hemostatic belt.
Figure 19:
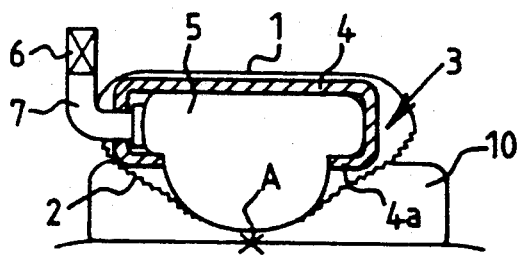
FIG. 19 is a longitudinal sectional view showing the compressive portion after injection of fluid into the compressive hemostatic belt.

FIGS. 17 through 19 show another embodiment of the invention which is the same as the compressive hemostatic belt of FIGS. 1 through 5 except for the following. Like reference characters are applied to like parts to omit a repetitive description thereof.

The compressive hemostatic belt of the invention is characterized in that the bowl shape of the rigid case 4 is modified to provide a flat pot adapted to hold the balloon 5 and having an inner flange 4a formed thereon at the opening to prevent the balloon from sticking out. With this arrangement, even if the strip 1 is wrapped so that a portion thereof is subjected to a force, as shown in FIG. 19, the balloon 5 is expanded toward the catheter insertion wound A. The protruding of the balloon 5 is controlled by the inner flange 4a of the rigid case 4. Thus, since there is no possibility of the rigid case 4 floating to deviate from the normal position, the catheter insertion wound A can be reliably compressed through the gauze 10 to completely stop the bleeding from the catheter insertion wound A.

Figure 20:
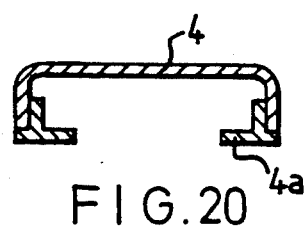
FIG. 20 is a longitudinal sectional view of another example of the rigid case used for the compressive hemostatic belt.

In addition, in the above embodiment, the inner flange 4a of the rigid case 4 is integrally formed, but the invention is not limited thereto. As shown in FIG. 20 the inner flange 4a may be a doughnut-shaped separate part having its compressive area cut out and may be attached to the open end by suitable attaching means such as screwing, fitting, bonding or welding. In the case where the inner flange 4a is removably attached to the rigid case 4, several inner flanges respectively having their different compressive areas cut out are prepared so that by changing them as the need arises, the compressive area for the patient can be easily adjusted.

In the above embodiment, the rigid case 4 is made of synthetic resin, but it may be formed of leather, thick nonstretch textile fabric or the like.

Another embodiment of the invention will now be described with reference to FIGS. 21 and 22.

Figure 21A:
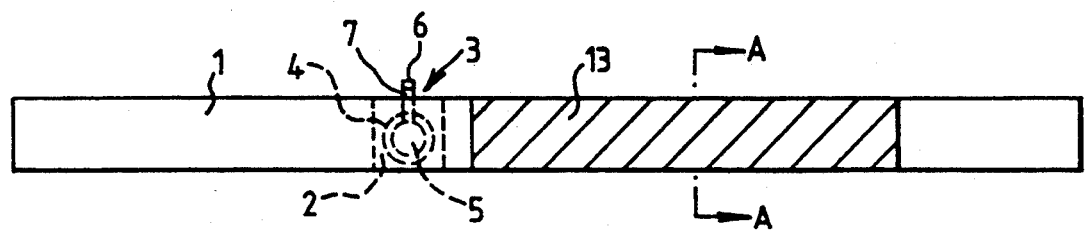
FIG. 21(a) is a plan view of the compressive hemostatic belt of the present invention.
Figure 21B:
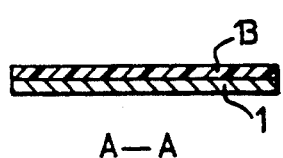
FIGS. 21(b), (c), and (d) are sectional views taken along the line A—A in FIG. 21(a)
Figure 21C:
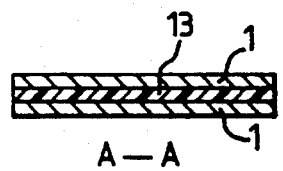
Figure 21D:
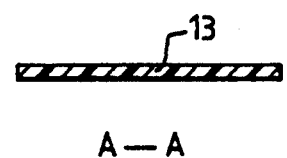
Figures 22A, 22B:
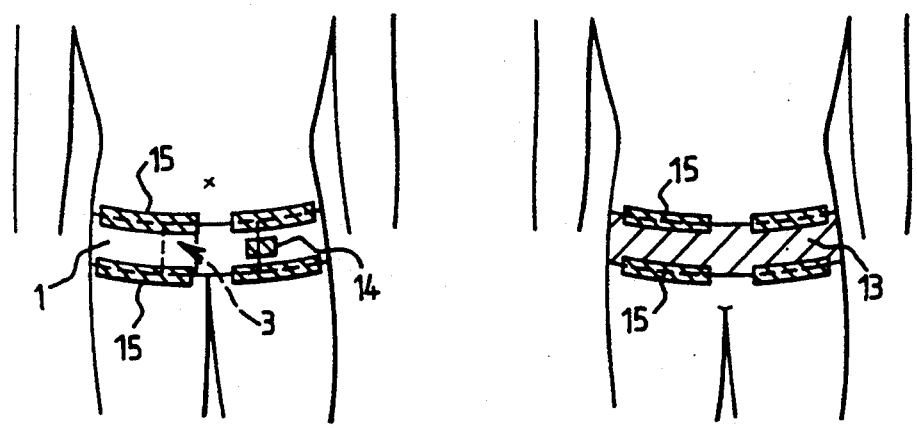
FIG. 22(a) is a front view of a human body showing how the compressive hemostatic belt of the invention is used.
FIG. 22(b) is a rear view of a human body showing how the compressive hemostatic belt of the invention is used.

FIG. 21(a) is a plan view of a compressive hemostatic belt. As in the case of the conventional article shown in FIG. 3, this compressive hemostatic belt comprises a strip 1 of nonstretch textile fabric and a fabric 2 in the form of a stretch textile fabric sewn to the strip 1 at a predetermined position to form a pocket 3, and a rigid case 4 a balloon 5 received in the pocket 3. Further, the rigid case 4 is received with its open side directed to the fabric 2 and the balloon 5 is received in the rigid case 4 such that a fluid feed tube 7 having a check valve 6 projects out of the pocket 3.

In the present invention, at least the portion of the strip 1 which covers the region extending from the waist to the hip when it is wrapped around the body has mounted thereon a reinforcing sheet 13 made of cardboard, PET, vinyl, rubber or fabric. The reinforcing sheet 13 is about 10 to 90 cm long and it is mounted on one side of the pocket 3 at a suitable position. Thereby, it does not develop wrinkles or kinks during wrapping operation, and the strip 1 can be firmly wrapped without having to apply much force. Further, by suitably changing the material, area and mounting position of the reinforcing sheet 13, the degree of tightness of wrapping can be adjusted, so that the compressive hemostatic belt is suited to various body types of patients (i.e.,) slim and fat persons and (children.) In addition, in the case where the length of the reinforcing sheet is not more than 10 cm, almost no reinforcing effect is developed and if it is not less than 90 cm, it tends to stick out of the strip 1.

The way the compressive hemostatic belt constructed in the manner described above is used will now be described.

First, as in the case of the conventional article shown in FIG. 3(c), the gauze 10 is placed on the catheter insertion wound 11 subsequent to the catheter examination and the pocket 3 is placed thereon with the fabric 2 directed to the wound 11. Afterwards, as shown in FIG. 2, the strip 1 is wrapped around the patient's waist and the end is locked as by a fabric adhesive plaster 14, while a fabric adhesive plaster 15 is applied to a portion of the body and the strip 1 to prevent deviation. Thereafter, a manually operable pump 8 and a pressure gauge 9 are connected to the fluid feed tube 7 of the balloon 5, and a liquid (including gels), or air, nitrogen gas, carbon dioxide gas or other gas is injected into the balloon 5 to expand the latter to compress the wound 11.

In addition, the reinforcing sheet 13, as shown in FIG. 21 (b), is mounted on the opposite surface of the strip 1 which contacts the body as by such means as a two-surface tape or sewing. Alternatively, as shown in FIG. 21 (c), the portion of the strip 1 associated with the reinforcing sheet 13 may be of double construction with the reinforcing sheet 13 placed in the clearance therebetween. Alternatively, as shown in FIG. 21 (d), the reinforcing sheet 13 may be connected to the end of the strip 1 to construct the reinforcing portion entirely of the reinforcing sheet 13.

What is claimed is:

1. A compressive hemostatic belt system, comprising:
   a mounting strip for binding a patient, said strip being formed from at least one of a non-elastic and a low-elastic material;
   an inflatable bag mounted in said strip and positioned so as to compress a selected area of the body of the patient when inflated, said bag having means for inflating said bag with fluid; and
   inflation directing means formed with said bag, for directing inflation of said bag, wherein the inflation of said bag is controlled so as to be directed substantially only toward the selected area of the body and prevented from inflating away from the body, wherein
   said mounting strip includes a pocket holding said bag and said inflation directing means, the pocket being formed with a contact side surface positioned so as to contact with the selected area of the body of the patient and formed from an elastically expandable sheet material.

2. A compressive hemostatic belt system as claimed in claim 1, wherein said inflation directing means includes a hard case member positioned on an outer side surface of said bag so as to prevent inflation of the outer side of said bag and to induce inflation of substantially only an inner inflating side of said bag.

3. A compressive hemostatic belt system as claimed in claim 2, wherein said inflation directing means includes a doughnut-shaped flange positioned with the hard case member between said bag and a contact side surface of the pocket, a hole in the doughnut-shaped flange being positioned so as to allow inflation of said bag through the hole.

4. A compressive hemostatic belt system as claimed in claim 1, wherein said inflation directing means includes bellows formed with an inner inflating side of said bag so as to induce inflation of substantially only the inner inflating side of said bag.

5. A compressive hemostatic belt system as claimed in claim 1, wherein the contact side surface of the pocket of said mounting strip is formed with a hole defined so as to allow inflation of said bag through the hole so as to contact with the selected area of the body of the patient.

6. A compressive hemostatic belt system as claimed in claim 1, further comprising:
   a fluid feed pump with a pressure gauge detachably connected to said bag through a check valve.

* * * * *